United States Patent [19]

Michelson

[11] Patent Number: 5,423,842
[45] Date of Patent: Jun. 13, 1995

[54] SPINAL MICROKNIFE

[76] Inventor: Gary K. Michelson, 438 Sherman Canal, Venice, Calif. 90291

[21] Appl. No.: 147,042

[22] Filed: Nov. 1, 1993

Related U.S. Application Data

[63] Continuation of Ser. No. 892,384, May 27, 1992, abandoned, which is a continuation of Ser. No. 480,653, Feb. 15, 1990, abandoned, which is a continuation of Ser. No. 194,301, May 16, 1988, abandoned.

[51] Int. Cl.⁶ .......................................... A61B 17/32
[52] U.S. Cl. ................................. 606/167; 30/294
[58] Field of Search .............. 606/125, 160, 170, 167, 606/138, 79; 30/DIG. 8, 294, 289, 290

[56] References Cited

U.S. PATENT DOCUMENTS

| | | | |
|---|---|---|---|
| 1,546,975 | 7/1925 | Feller | 30/294 X |
| 2,878,809 | 3/1959 | Treace | 606/170 |
| 3,600,806 | 8/1971 | Naccash | 30/294 |
| 3,610,246 | 10/1971 | Salmon | 606/167 |
| 3,673,687 | 7/1972 | Phillips et al. | 30/294 |
| 4,071,029 | 1/1978 | Richmond et al. | 606/180 |
| 4,098,157 | 7/1978 | Doyle | 606/138 |

FOREIGN PATENT DOCUMENTS 2851239 3/1980 Germany .
993929 2/1983 U.S.S.R. .

OTHER PUBLICATIONS

Noel L. Mills et al. "Valvulotomy of Valves in the Saphenous Vein Graft Before Coronary Artery Bypass" Jun., 1976.

*Primary Examiner*—Michael H. Thaler
*Attorney, Agent, or Firm*—Lewis Anten; Amedeo Ferraro

[57] ABSTRACT

An improved microknife for use in spinal surgery is disclosed which simplifies the procedure for performing an anterior cervical discectomy, while reducing the possibility of penetrating the dural sac or injuring the spinal cord.

6 Claims, 2 Drawing Sheets

SPINAL MICROKNIFE

This application is a continuation of application Ser. No. 07/892,384, filed on May 27, 1992, now abandoned which is a continuation of application Ser. No. 07/480,653, filed on Feb. 15, 1990, now abandoned which is a continuation of application Ser. No. 07/194,301, filed on May 16, 1988 now abandoned.

BACKGROUND

The present invention relates to micro surgical instruments, and in particular, to micro surgical instruments that are used in spinal surgery.

The use of this instrument is for microsurgery, as in an anterior cervical discectomy where one is removing the disc from between the cervical vertebrae. In a disc herniation, the disc may fragment and go out the back of the annulus (sequester) and yet remain superficial to the posterior longitudinal ligament, the ligament, which runs from vertebrae to vertebrae at the most posterior aspect of the bodies, or it may pierce the posterior longitudinal ligament and come to lie between the posterior longitudinal ligament and the dural sac containing the spinal cord.

Cutting in a downward motion on top of the dural sac containing the cerebrospinal fluid and spinal cord would be extremely dangerous. Even cutting the dural sac without damaging the spinal cord directly causes a very serious problem in that leak in this area is extremely difficult, if not impossible, to repair as there is no room available for suturing.

Therefore, at the present time, there is no easy way to get through the tissues of the posterior longitudinal ligament, or for that matter the posterior annulus when going after sequestered disc fragments. The current state of the art is to use either a micro hook which is nothing more than a button hook type device on a very small scale of one to two millimeters, which is then used to slowly pick away at the fibers of the posterior longitudinal ligament, which is a tedious task. One then uses the small hook to fish blindly behind the ligament for the suspected disc fragment. As the area behind the posterior longitudinal ligament is not visualized one can never be certain as to whether any disc material is there to begin with or still remains. This may result in wasted time on the one hand, or inadequate removal with a poor result on the other.

An alternative method used, at the present time is to take a kerrisson rongeur which is a rongeur which cuts with an up and down motion and to try to put the foot of the rongeur deep to the posterior annulus and posterior longitudinal ligament and then to cut what is between the jaws. There are at least two problems associated with this. The first is that the deep portion of the jaw is in a blind area so that one can not be sure what else is being cut and secondly, frequently there is a tearing rather than a cutting of the tissue. The fact that one is working through a deep and narrow opening limits significantly the available options for removing this tissue. A blade which cuts by safely passing beneath tissue and cutting only on its upper visible surface is a dramatic improvement from the current state; and would be of great value in other applications of microsurgery such as intracranial neurosurgery.

BRIEF SUMMARY OF THE INVENTION

The microknife of the present invention provide an offset handle which will allow unobstructed visualization of the cutting portion of the blade when operating on a cervical disc with an operating microscope or with the use of high powered ocular magnification. The design of the blade tip has a smooth slightly biplanar convex bottom surface and a concave upper cutting surface, comparable to a cowcatcher on the front of a train, which will slip underneath the tissues to be cut, lifting the tissue onto the upper cutting portion of the blade which is perpendicular to the convex bottom surface. Therefore the posterior longitudinal ligament is lifted away from the dural sac prior to being cut by the upper cutting surface of the microknife.

OBJECTS OF THE PRESENT INVENTION

It is an object of the present invention to provide an improved microknife which is safer to use.

It is another object of the present invention to provide an improved microknife which is easier to use.

It is another object of the present invention to provide an improved microknife which provides a better field of view.

It is another object of the present invention to provide an improved microknife which performs quicker.

These and other objects of the present invention will be apparent from a review of the following specification and the accompanying drawings.

DETAILED DESCRIPTION OF THE DRAWINGS

Figure 1:
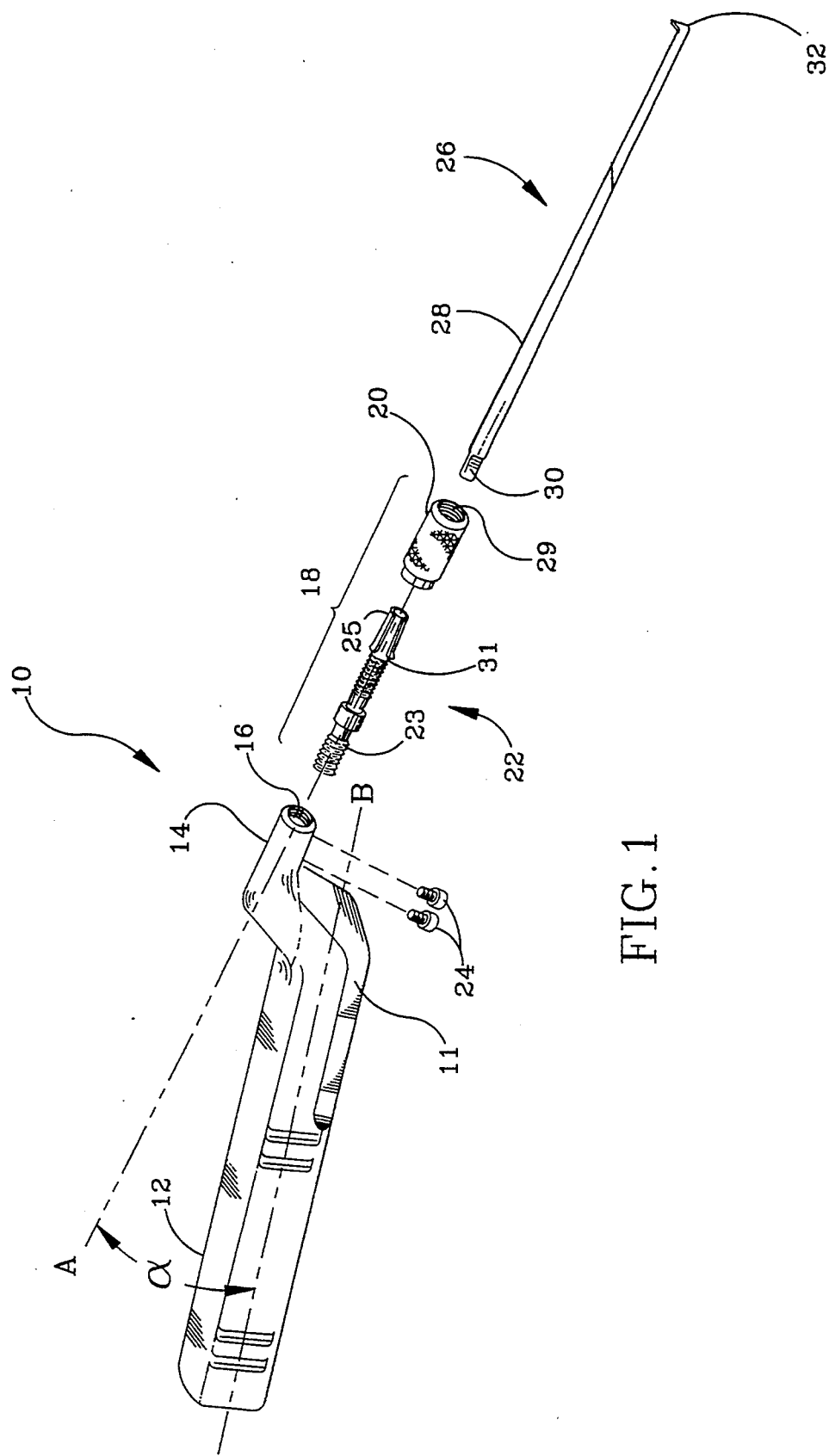
FIG. 1 is an exploded perspective view of the present invention.
Figure 2:
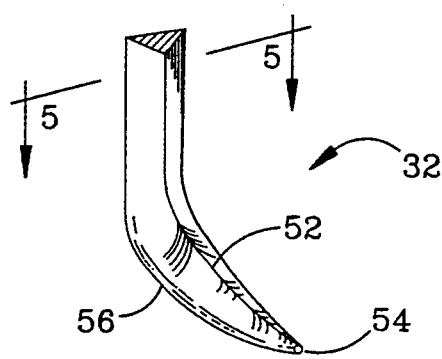
FIG. 2 is an enlarged perspective view of the microknife blade.

Referring to the FIG. 1 the microknife 10 is shown in an exploded view. The microknife 10 has a handle 12 having a generally rectangular solid configuration. At on end thereof 11 is an offset attachment assembly portion 14 which comprises an internally threaded member 16 for receiving the microknife member 26. The attachment assembly is offset from the axis of the handle so that the central axis A of the internal threaded portion is offset from the central axis B of the handle 12 by about 20-30 degrees.

A compression assembly 18 consists of an external collar 20 and an internal compressed member 22. One end of the internal compressed member 22 has complementary threads 23 for engaging the threads of the internal threaded portion 16 of the handle. The other end of the compressed member has a spaced opening 25 for receiving the irregular end 30 of the slender rod 28 that terminates in the microknife blade 32. the collar 20 has internal threads 29 that engage the external threads 31 proximate the spaced opening 25. The diameter of the compressed member increases away from the spaced opening 25.

The device is easily assembled by screwing the compression assembly 18 into the internally threaded member 16. The irregular end 30 of the rod 28 is inserted in the spaced opening 25, and collar 20 turned, tightening the compression member 18 to fix the rod 28 in place.

In the preferred embodiment, the angle between the central rod 18 and the handle 12 is between 0-20 degrees, preferrably 12 ½ degrees. However, the angle may be changed so the line of sight is acceptable to the particular user, and the microknife blade 32 at the other end of the rod 28 may be easily manipulated.

The lower end of the rod 28 above the microknife blade 32 is triangular in cross section in order to provide an increased field of view.

The microknife rod 28 consists of a long slender rod about 6 inches long and having a diameter of about 1/16-⅛ inches. One end of the rod 28 has an irregular cross section portion 30 at one end and an offset microknife blade 32 at the other end.

Figure 3:
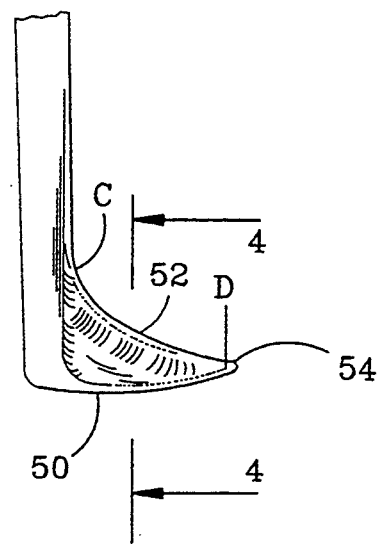
FIG. 3 is a side view of the enlarged microknife.

Referring to FIGS. 2-5 the present invention, the microknife blade 32 is shown in an expanded view. The microknife blade 32 is fixed substantially perpendicular to the main axis of rod 28. The microknife blade itself 32 has a slightly biplanar convex smooth bottom surface 50 and a sharp upper concave surface 52. As seen in FIG. 3, bottom surface 50 is curved in a first plane the bottom surface curves upward at on end. The sharp upper surface 52 is slopped in a parabolic configuration from the rod C to the point O just before the tip 54 of the blade.

Figure 4:
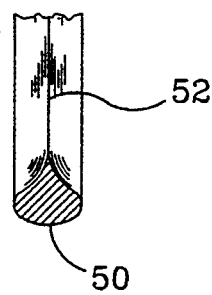
FIG. 4 is an end sectional view of the microknife taken along lines 4—4 of FIG. 3.
Figure 5:
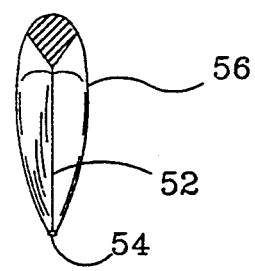
FIG. 5 is a top section view of the microknife taken along lines 5—5 of FIG. 2.

Referring to FIGS. 4 and 5 it may be seen that the upper sides of the blade 56 Taper outwardly from cutting edge at the top 54 and increases in width from front to back, blending into the smooth bottom surface 50.

The portion of the blade 32 between C and D provides the cutting action, much like running a sharp scissors along a piece of paper. The blunt tip 54 prevents puncturing and the smooth bottom surface 50 permits the microknife blade 32 to easily glide along on top of the dural sac, cutting the tissues as it proceeds. Thus, the device operates much in the same manner as a cow catcher, avoiding damage to anything beneath the blade, and permitting a smooth safe and quick cutting operation.

The particular design of the knife blade itself allows for a safe way of cutting broadly across the posterior annulus and or the posterior longitudinal ligament thus allowing full visualization of that space back there and the removal of any sequestered disc material under direct visualization.

In use, the tip 54 of the blade is inserted in the opening. Because the tip 54 is blunt, it will not puncture the dural sac. The tip 54 is sloped in an upward manner portion so that the convex, smooth bottom portion 50 lies on top of the sac. As the blade is glided forward, the tissue to be cut is lifted by the blunt tip 54 until the tissue comes into contact with the sharp upper cutting surface 52, which cuts the tissue. The wedge shape of the blade 32 pushes the cut tissue out of the way.

While the invention has been described with regards to the preferred embodiment, it is recognized that alternative embodiments may be devised which do not depart from the present invention. For example, different methods of attaching the blade to the handle assembly and different handles may be used equally as well.

What I claim is:

1. A surgical microknife for use in surgical procedures comprising a tip mounted substantially at 90 degrees at one end of a rod having a longitudinal axis and a handle at the other end of said rod, said tip having a blunt end, a parabolic upper portion along substantially the entire length of said tip having a sharp cutting edge along said parabolic upper portion of said tip, a pair of concave side walls, each of said pair of side walls sloping outwardly from each other a distance greater than the width of said cutting edge from said cutting edge to a blunt lower convex portion below said cutting edge, said tip tapering from a large generally triangular cross section area portion proximate the juncture of said rod and said tip to a narrower generally triangular cross section area approaching said blunt end of said tip, said blunt end being below said cutting edge when said rod is oriented vertically, and said blunt lower convex portion having an arcuate bottom, said arcuate bottom being arcuate in multiple planes along substantially the entire length of said tip, said arcuate bottom being curved in a first plane which is coplanar with said tip and said longitudinal axis and being curved in a second plane which is perpendicular to said first plane and parallel to said longitudinal axis whereby movement of said tip in a direction substantially 90 degrees to said longitudinal axis of said rod causes lifting and cutting.

2. The device of claim 1, in which said handle has means for retaining said rod at an angle in relationship to the long axis of the handle.

3. The device of claim 2 in which said angle is less than 20 degrees.

4. The device of claim 3 in which said angle is approximately 12½ degrees.

5. The device of claim 2 in which a portion of said rod proximate said juncture of said tip and said rod is non circular in cross section.

6. The device of claim 7 in which said cross section of said rod proximate said juncture of said tip and said rod is triangular.

* * * * *